Figure 1:
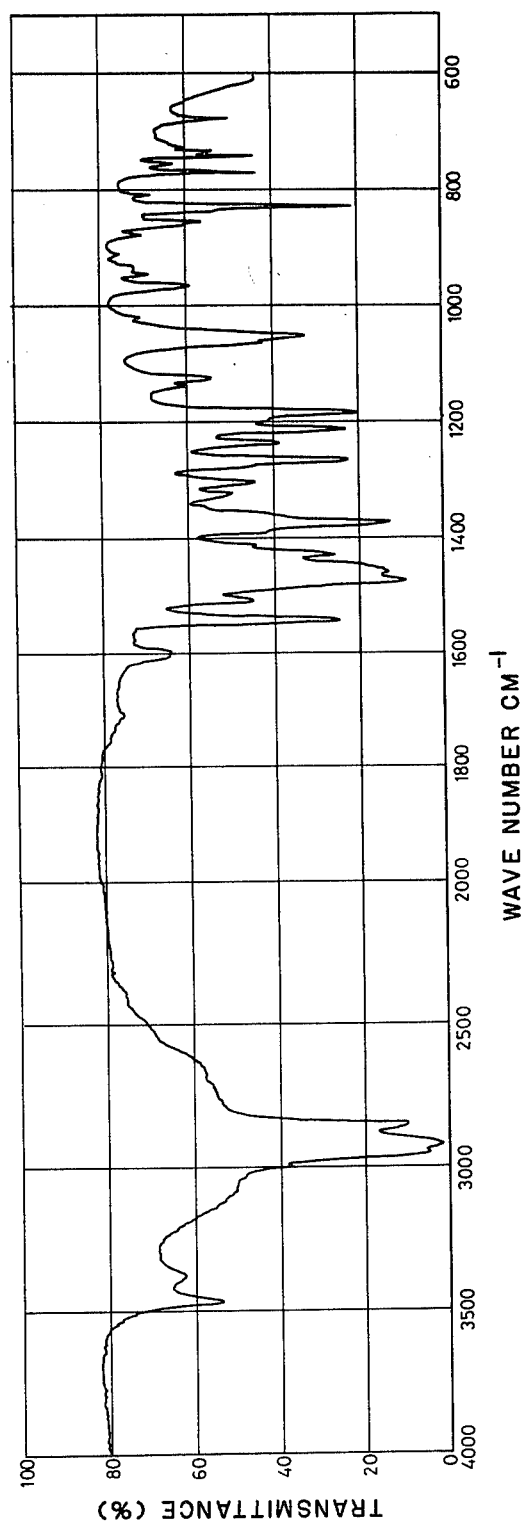

United States Patent [19]

Bononi

[11] Patent Number: 4,463,012

[45] Date of Patent: Jul. 31, 1984

[54] NITROIMIDAZOLES HAVING TRICHOMONACIDAL ACTIVITY AND PHARMACEUTICAL COMPOSITIONS THEREOF

[76] Inventor: Loris J. Bononi, Castiglione del Terziere, 54020, Gabbiana (Massa Carrara), Italy

[21] Appl. No.: 370,651

[22] Filed: Apr. 21, 1982

[30] Foreign Application Priority Data

Apr. 21, 1981 [IT] Italy .............................. 21298 A/81

[51] Int. Cl.³ .................. A61K 31/415; C07D 233/94
[52] U.S. Cl. ................................ 424/273 R; 548/338; 548/339
[58] Field of Search ............................. 548/338, 339; 424/273 R

[56] References Cited

FOREIGN PATENT DOCUMENTS 1427761 1/1966 France ................................ 548/339
2436780 4/1980 France ................................ 548/338

OTHER PUBLICATIONS

March, J., *Advanced Organic Chemistry*, McGraw Hill, New York, 1968, pp. 684–687.
Chemical Abstracts, 63: 18097b (1965), [Neth. Appl. 6,413,814, 5/28/65.]

*Primary Examiner*—Richard A. Schwartz
*Attorney, Agent, or Firm*—Pollock, Vande Sande & Priddy

[57] ABSTRACT

The nitroimidazoles having general formula:

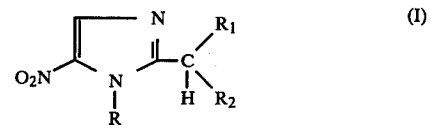

(I)

wherein R represents alkyl $C_1$–$C_5$, hydroxyalkyl $C_1$–$C_5$, an alkylsulfonyl group, an aminoalkyl group, wherein the alkyl contains 1 to 5 carbon atoms and the amino group is the radical of a secundary or tertiary, linear or cyclic amine; $R_1$ is —OH and $R_2$ represents the group:

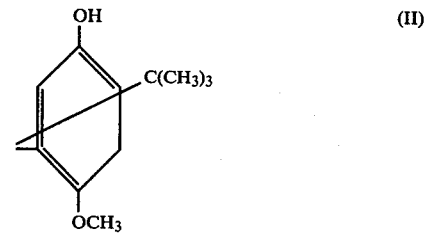

(II)

the tert-butyl substituent —$C(CH_3)$ being in the 3, 4 or 6 position of the anisole ring or $R_1$ and $R_2$ both represent the above indicated group (II), are endowed with activity against pathogenic protozoa and bacteria, particularly as regards *Trichomonas vaginalis*.

The subject compounds are prepared by reacting a halo-magnesium derivative of tert-butyl-4-hydroxy-anisole and 5-nitro, 1-R substituted, 2-formyl-imidazole.

9 Claims, 3 Drawing Figures

NITROIMIDAZOLES HAVING TRICHOMONACIDAL ACTIVITY AND PHARMACEUTICAL COMPOSITIONS THEREOF

The present invention relates to nitroimidazole compounds having general formula:

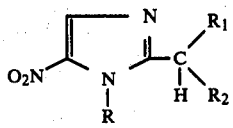

wherein R represents alkyl having 1 to 5 carbon atoms, hydroxyalkyl having 1 to 5 carbon atoms, an alkyl-sulfonic group, an amino-alkyl group in which the alkyl contains 1 to 5 carbon atoms and the amino group is the radical of a secundary or tertiary, linear or cyclic amine; $R_1$ represents —OH and $R_2$ is the group

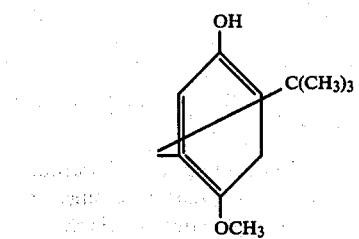

the tert-butyl substituent $C(CH_3)_3$ being in the position 3, 4 or 6 of the anisole ring, or $R_1$ and $R_2$ both represent the above indicated group (II).

More specifically the present invention relates to compounds having general formula:

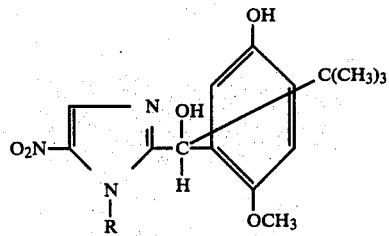

wherein R has the above indicated meaning.

It has now been found that the nitroimidazoles having formula (I) and (III) are endowed with anti-protozoal (particularly trichomonacidal) and antibacterial activity (particularly against anaerobic micro-organisms), and at the same time do not show mutagenic activity. Consequently, the compounds of the present invention are useful in the treatment of the diseases of protozoal and bacterial nature, such as for instance the trichomoniasis in its several forms, amoebiasis, giardiasis, and the infections induced from anaerobic bacteria in the several forms.

Referring for illustrative purpose to the trichomoniasis, it is to be considered a contagious infective disease of relevant social importance; it is in fact enough to take into account that about 20% of the world female population is affected by vaginal trichomoniasis.

Relevant efforts have been and are put forth in searching for trichomonacidal agents, having both systemic and local action, which are very efficacious and non-toxic and which, when administered to pregnant women, do not influence the regular development of the fetus.

Furthermore, the trichomonoacidal agent should not adversely effect the natural equilibrium of the vaginal bacterial flora, including Bacillus Döderlein (*Lactobacillus acidophilus*).

Among the compounds to date known and proposed for the treatment of trichomoniasis the following can be cited:

(a) 1-(2-hydroxyethyl)-2-methyl-5-nitroimidazole (Jacobs et al, U.S. Pat. No. 2,944,641), also known under the name of metronidazole; however it has not been found to be completely satisfactory, since certain strains of *Trichomonas vaginalis* developed a resistance to the action thereof.

(b) 2-(2-vinylsubstituted)-5-nitroimidazoles, substituted in the 1 position with a lower alkyl, (Miller et al, U.S. Pat. No. 3,549,626), useful also as intermediates for antiprotozoal agents containing sulfur.

(c) Derivatives of 2-(5-nitro-2-furyl)-vinylpyrimidine (Minami et al, U.S. Pat. No. 3,464,982).

(d) In the U.S. Pat. No. 3,882,105 there is disclosed and claimed the use, for the treatment of diseases induced from protozoa and of bacterial infections, particularly as trichomonacidal agent, of 2-amino-4-[2-(1-lower alkyl-5-nitro-2-imidazolyl)-vinyl]-pyrimidine.

It is worth to note that all the nitroimidazole compounds to date used in therapy show mutagenic activity.

For the preparation of the compounds of formula (I) the present invention provides a process which is characterized in that a 5-nitro, 1-R substituted, 2-formyl-imidazole is reacted in an organic solvent with a halo-megnesium derivative of tert-butyl-4-hydroxyanisole, the molar ratio between the two reactants being 1:1 or 1:2 depending on the fact that a compound of formula (I) is desired in which one or respectively two groups of formula (II) are present.

The following examples illustrate, in non limiting way, the preparation of compounds according to the invention.

EXAMPLE 1

5-nitro-1-methyl-imidazolyl-3-tert-butyl-5-hydroxy-2-methoxy-phenyl-carbinol having the formula:

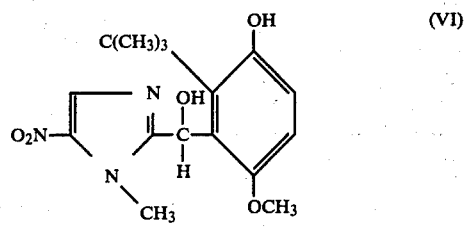

18 g (0.1 moles) of tert-butyl-4-hydroxyanisole in 100 mls of tetrahydrofuran are added dropwise, under nitrogen and by cooling at a temperature of about 15° C., to a solution of 0.1 moles (40 mls) of $CH_3MgCl$ in 60 mls of tetrahydrofuran.

Upon the addition is completed 200 mls of benzene are added and the mixture is evaporated at a temperature of 40°–50° C.

There are then added further 200 mls of benzene and the mixture is evaporated to a reduced volume; the concentrated solution is brought to a volume of 220 mls with benzene and then dropwise supplemented with 15.5 g (0.1 moles) of 5-nitro-1-methyl-2-formyl-imidazole in 100 mls of benzene, keeping thereafter the mixture for one night at room temperature.

After neutralization with diluted hydrogen chloride two phases are separated, the aqueous one being disposed to waste, whereas the organic phase is brought to about dryness.

Figure 2:
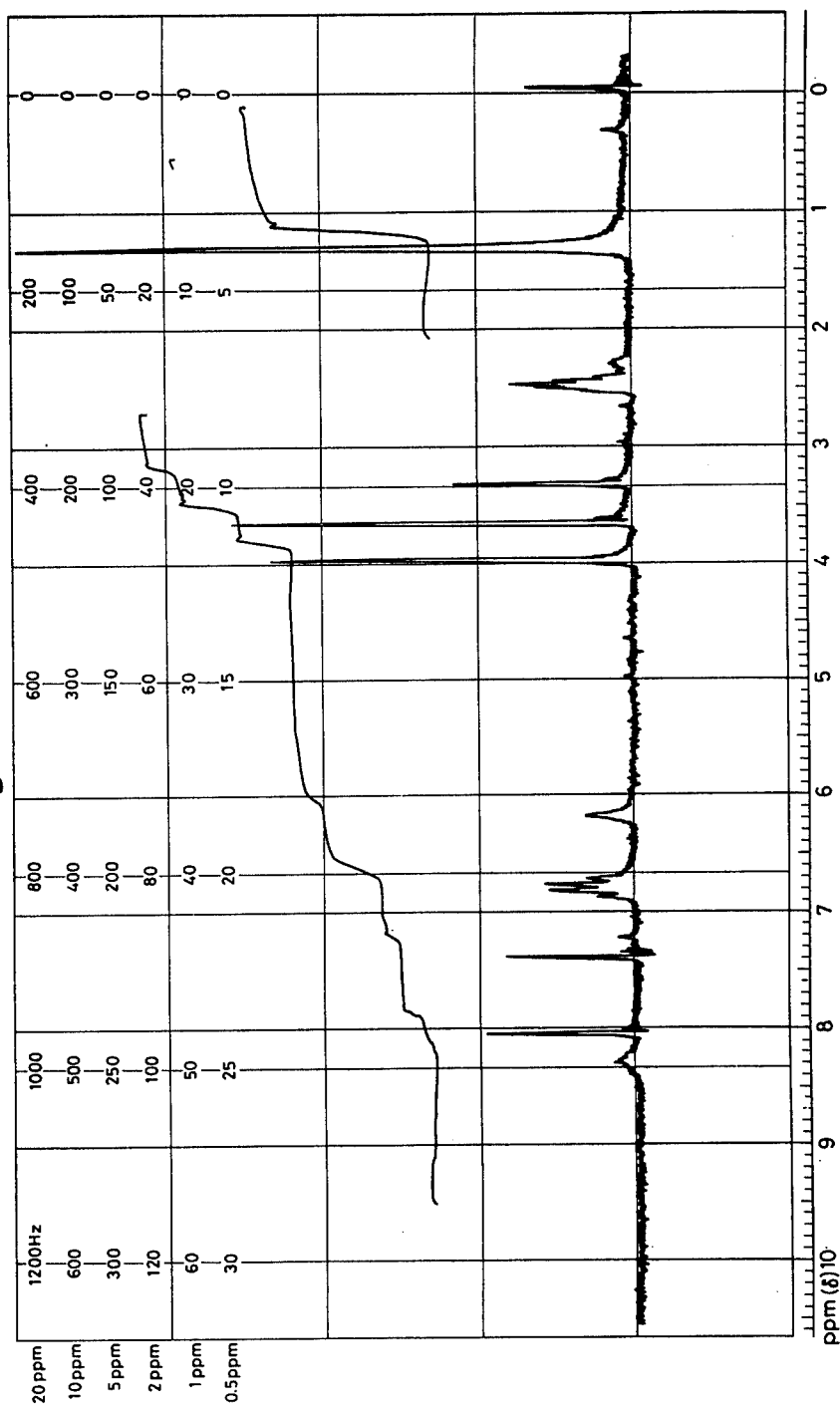

The mass is taken with acetone, decolored with active carbon and kept on standing for a night. There are obtained 4 g of amorphous yellowish product, having melting point 125°–128° C., which show the IR spectrum of FIG. 1 and the NMR spectrum of FIG. 2. These spectra correspond to the structure as foreseen.

EXAMPLE 2

5-nitro-1-methyl-imidazolyl-bis-(3-tert-butyl-5-hydroxy-2-methoxy-phenyl)-methane having the formula

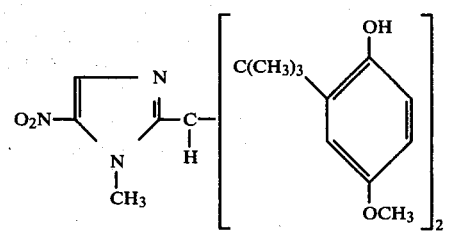

(VII)

The example 1 is repeated, apart that instead of 0.1 mole of tert-butyl-4-hydroxyanisole there are used 0.2 moles of the same compound and likewise the amount of CH$_3$MgCl is increased to 0.2 moles.

The resulting product, having the formula (VII), melts at 305° C. with decomposition.

Figure 3:
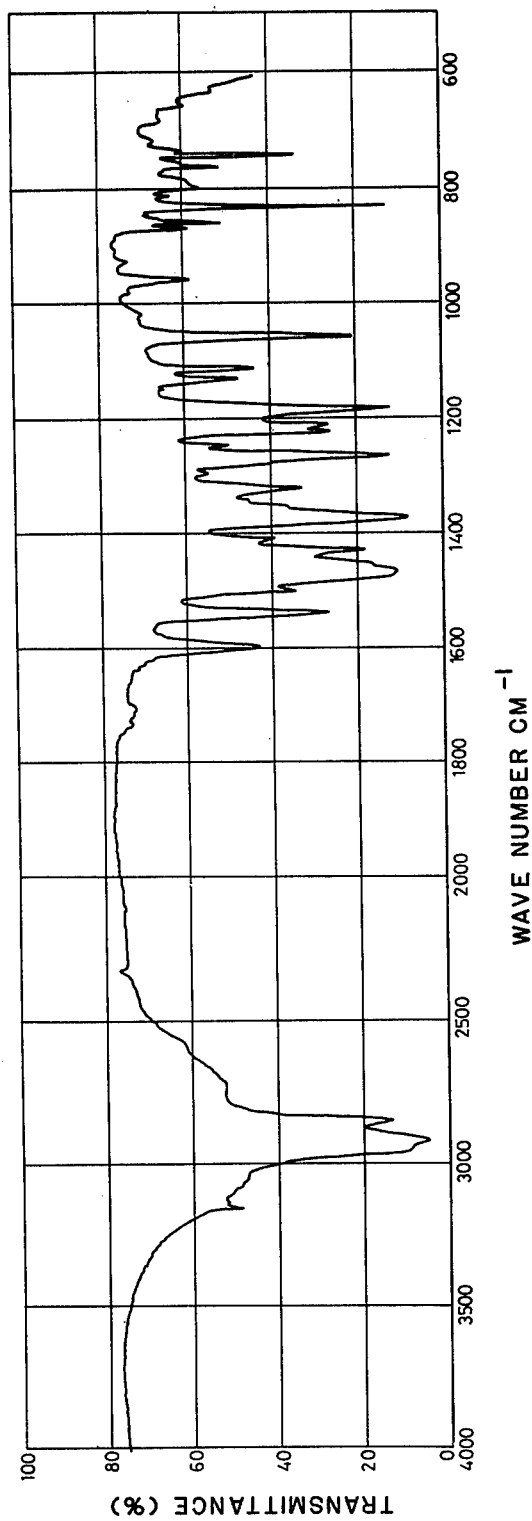

The FIG. 3 shows the IR spectrum of the thus obtained compound.

The compound of example 1 has been tested as regards the toxicity and the activity, the results confirming the possibilities of therapeutical use.

Particularly, it has been found that it shows:
LD$_{50}$ per os in the mouse: 6100 mg/kg±19%
LD$_{50}$ per os in the rat: 6800 mg/kg±20%.

The in vitro activity of the compound (as evaluated against several strains of *Trichomonas vaginalis*) is on the average 0.6 mcg/ml.

The mutagenic activity at the Ames test (with and without metabolics activation) is absent.

Preliminary studies of kinetics in the dog have been carried out in comparison with 2-amino-4-[2-(1-methyl-5-nitro-2-imidazolyl)-vinyl]-pyrimidine; it was found that:

(1) the average life of the compound of the invention is about two times that of the comparison compound.

(2) The elimination takes place by about 40% through the urines and by about 60% through the feces.

(3) The presence of metabolites (not yet identified) in the urines and in the blood amounts of about 5%.

(4) The antibacterial spectrum is like that of metronidazole.

The other compounds having the above formula (III) show a behaviour like that already described, namely the absence of mutagenic power and an LD$_{50}$ value per os in the mouse and in the rat of between 5000 and 7000 mg/kg, and in vitro activity against *Trichomonas vaginalis* of between 0.6 and 1.0 mcg/ml.

Lastly, also for the compounds of formula (I) in which both R$_1$ and R$_2$ represent a group (II), as the compound of example 2, the in vitro activity against *Trichomonas vaginalis* is about 0.6 mcg/ml and the LD$_{50}$ per os in the mouse in 7300 mg/kg ±20%.

The compounds of the present invention, besides the use as trichomonoacidal agents, are active against the most important anaerobic bacteria.

For the use of the compounds of the present invention the forms and formulations already known and used for the known trichomonoacidal agents are contemplated, and like dosages of active compound are foreseen for the therapeutical administration.

I claim:

1. Nitroimidazole derivative having formula:

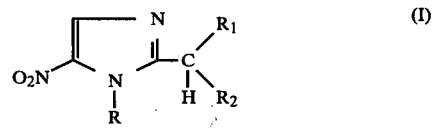

(I)

wherein R represents an alkyl having 1 to 5 carbon atoms, hydroxyalkyl having 1 to 5 carbon atoms, an alkylsulfonic group, an amino-alkyl group in which the alkyl contains 1 to 5 carbon atoms and the amino group is the radical of a secondary or tertiary, linear or cyclic amine; R$_1$ is —OH and R$_2$ represents the group:

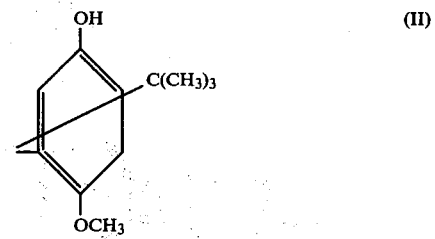

(II)

the tert-butyl substituent being in the 3, 4 or 6 position of the anisole ring, or R$_1$ and R$_2$ both represent the above indicated group (II).

2. 5-nitro-1-methyl-imidazolyl-3-tert-butyl-5-hydroxy-2-methoxy-phenyl-carbinol.

3. 5-nitro-1-methyl-imidazolyl-bis-(3-tert-butyl-5-hydroxy-2-methoxy-phenyl)-methane.

4. Pharmaceutical composition for the treatment of diseases induced from pathogenic protozoa and anaerobic bacteria comprising as active ingredient in an amount effective for the treatment of said diseases, a nitroimidazole derivative according to claim 1, and a pharmaceutically acceptable vehicle and a pharmaceutically acceptable excipient.

5. Composition according to claim 4, characterized in that said nitro-imidazole derivative is the compound 5-nitro-1-methyl-imidazolyl-3-tert-butyl-5-hydroxy-2-methoxy-phenyl-carbinol.

6. Composition according to claim 4, characterized in that said nitro-imidazole derivative is the compound of 5-nitro-1-methyl-imidazolyl-bis-(3-tert-butyl-5-hydroxy-2-methoxy-phenyl)-methane.

7. The composition of claim 4 wherein said active ingredient is present in an amount effective for the treatment of trichomoniasis.

8. The composition of claim 5 wherein said derivative is present in an amount effective for the treatment of trichomoniasis.

9. The composition of claim 6 wherein said derivative is present in an amount effective for the treatment of trichomoniasis.

* * * * *